(12) United States Patent
Shu et al.

(10) Patent No.: US 7,404,323 B2
(45) Date of Patent: Jul. 29, 2008

(54) CONCENTRATION DETECTOR AND FUEL SUPPLIER WITH SAID DETECTOR

(75) Inventors: Hsi-Ming Shu, Taipei (TW); Feng-Yi Deng, Taipei (TW); Yu-Lin Tang, Taipei (TW); Ya-Chien Chuang, Taipei (TW); Yi-Hsien Chen, Taipei (TW)

(73) Assignee: Antig Technology Co., Ltd., Taipei (TW)

( * ) Notice: Subject to any disclaimer, the term of this patent is extended or adjusted under 35 U.S.C. 154(b) by 9 days.

(21) Appl. No.: 11/562,083

(22) Filed: Nov. 21, 2006

(65) Prior Publication Data

US 2007/0113624 A1    May 24, 2007

(30) Foreign Application Priority Data

Nov. 23, 2005   (TW) ................. 094141053

(51) Int. Cl.
*G01N 9/00* (2006.01)
(52) U.S. Cl. ........................... 73/440; 73/454
(58) Field of Classification Search ................. 73/32 R, 73/61.41, 61.43, 61.44, 440, 451, 452, 454
See application file for complete search history.

(56) References Cited

U.S. PATENT DOCUMENTS

| | | | | | |
|---|---|---|---|---|---|
| 1,701,404 | A | * | 2/1929 | Dennis | 73/452 |
| 2,332,807 | A | * | 10/1943 | Moore | 73/452 |
| 2,891,403 | A | * | 6/1959 | Potter | 73/453 |
| 3,469,447 | A | * | 9/1969 | Becker | 374/116 |
| 4,353,253 | A | * | 10/1982 | Callahan | 73/454 |

\* cited by examiner

*Primary Examiner*—Hezron E. Williams
*Assistant Examiner*—John Fitzgerald

(57) ABSTRACT

A concentration detector is disclosed, which is adapted to detect a concentration of a liquid fuel in a container. The concentration detector includes a rotating means positioned underneath a level of a liquid fuel and rotatable at an angle θ on a X-Y plane. The rotating means includes at least three floating objects connected with each other. Each floating object has a specific gravity less than a specific gravity of the liquid fuel ρ. The floating objects are balanced according to a torque equation, $F(\theta,\rho)=0$, such that the rotating means is still under the level of the liquid fuel. While a concentration of the liquid fuel is changed and the angle θ of the rotating means is detected, the specific gravity of the liquid fuel ρ is obtained from the torque equation, $F(\theta,\rho)=0$, and thereby computing the concentration of the liquid fuel.

23 Claims, 5 Drawing Sheets

| the concentration of the methanol solution | the specific gravity of the methanol solution |
| --- | --- |
| 3 % | 0.9937 |
| 4 % | 0.9917 |
| 5 % | 0.9896 |
| 6 % | 0.9875 |
| 7 % | 0.9854 |
| 8 % | 0.9833 |
| 9 % | 0.9812 |
| 10 % | 0.9791 |
| 11 % | 0.9771 |
| 12 % | 0.9750 |
| 13 % | 0.9729 |
| 14 % | 0.9708 |
| 15 % | 0.9687 |

CONCENTRATION DETECTOR AND FUEL SUPPLIER WITH SAID DETECTOR

FIELD OF THE INVENTION

The present invention relates to a concentration detector, and more particularly, to a sensor for detecting the concentration of liquid fuels in a fuel cell.

BACKGROUND OF THE INVENTION

A fuel cell is a power generator, which converts chemical energy stored within fuel and oxidants directly into electrical energy through reactions of its electrodes. The different types of fuel cells are diverse and their classifications varied. According to the properties of their electrolytes, fuel cells can be divided into five types including alkaline fuel cells, phosphoric acid fuel cells, proton exchange membrane fuel cells, fused carbonate fuel cells, and solid oxide fuel cells. Wherein, a proton exchange membrane fuel cell includes a so-called direct methanol fuel cell (DMFC), which directly uses methanol as fuels without modifying the same into hydrogen gas. This is also at present a technique that can generate relatively high power. Such fuel cells may be applied to large power plants, vehicular power generators, portable power supplies, and so forth.

It is essential to control the concentration of liquid fuels while commercializing such fuel cells as DMFC. Theoretically, fuels with lower concentrations produce less electricity, and fuels with higher concentrations produce more electricity. Accordingly, to maintain the concentration at a predetermined level, a concentration detector is needed to monitor the concentration of fuels in real-time. As such, the electricity of fuel cells is qualified, and the electronic products using the cells will not be damaged due to the unsteady power supplied by the fuel cells.

SUMMARY OF THE INVENTION

It is a primary object of the invention to provide a concentration detector which constantly responds to the required concentration of liquid fuels for a fuel cell.

It is a secondary object of the invention to provide a fuel supply tank for a liquid fuel cell that employs a concentration detector to sense the concentration of liquid fuels in the fuel supply tank in real-time.

In accordance with the aforementioned objects of the invention, a concentration detector is provided, which is adapted to detect a concentration of a liquid fuel in a container. The concentration detector includes a rotating means positioned underneath a level of a liquid fuel and rotatable at an angle on an X-Y plane. The rotating means includes at least three floating objects connected with each other. Each floating object has a specific gravity less than a specific gravity of the liquid fuel $\rho$. The floating objects are balanced according to a torque equation, $F(\theta,\rho)=0$, such that the rotating means is still under the level of the liquid fuel. While a concentration of the liquid fuel is changed and the angle $\theta$ of the rotating means is detected, the specific gravity of the liquid fuel $\rho$ is obtained from the torque equation, $F(\theta,\rho)=0$, and thereby computing the concentration of the liquid fuel.

BRIEF DESCRIPTION OF THE DRAWINGS

The foregoing aspects, as well as many of the attendant advantages and features of this invention will become more apparent by reference to the following detailed description, when taken in conjunction with the accompanying drawings, wherein:

FIG. 3 shows a comparison table listing the relationship between the concentration and the specific gravity of the methanol solution.

DETAILED DESCRIPTION OF THE INVENTION

Figure 1A:
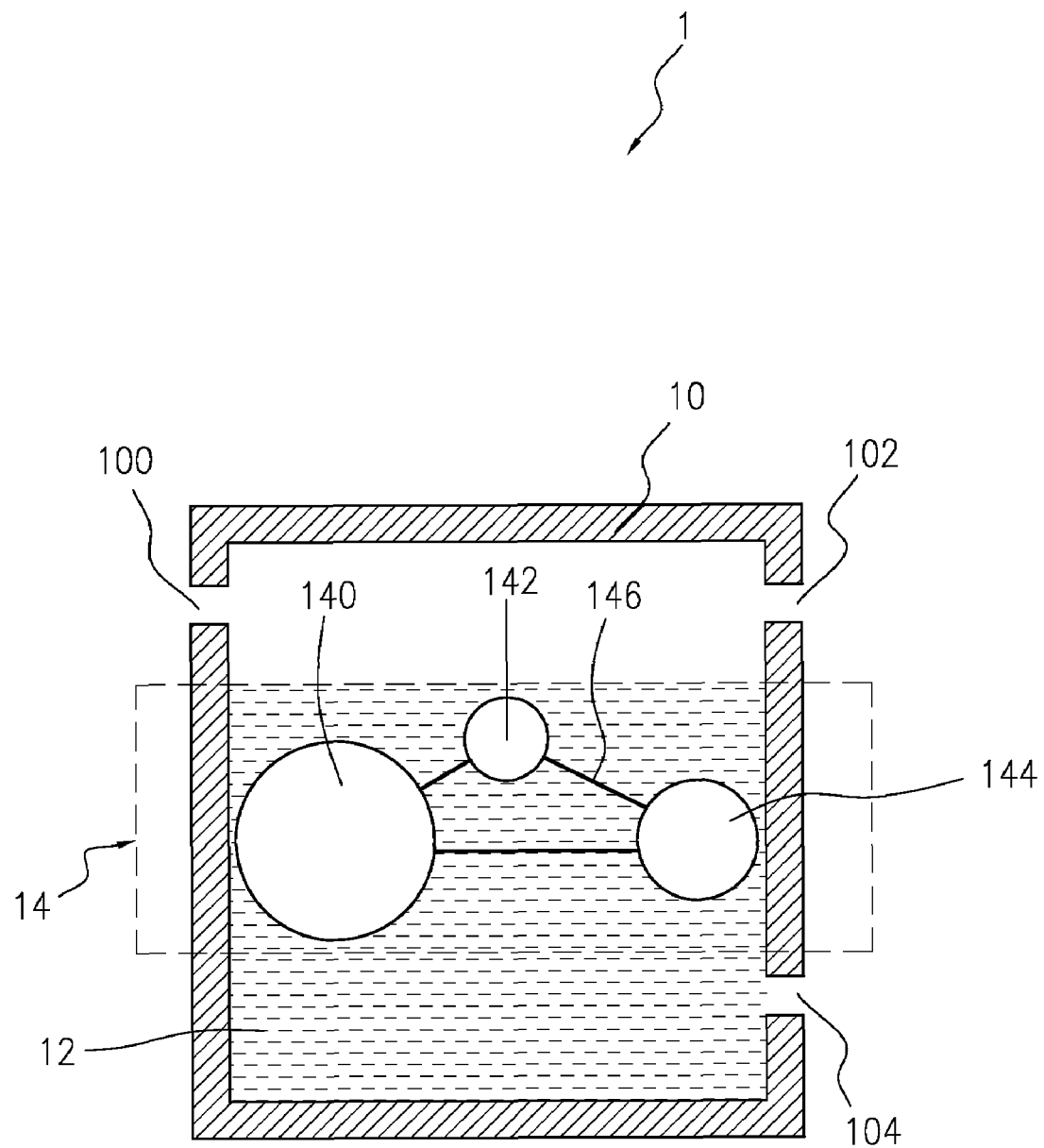
FIG. 1A is a side view of a concentration detector according to one embodiment of the invention.
Figure 1B:
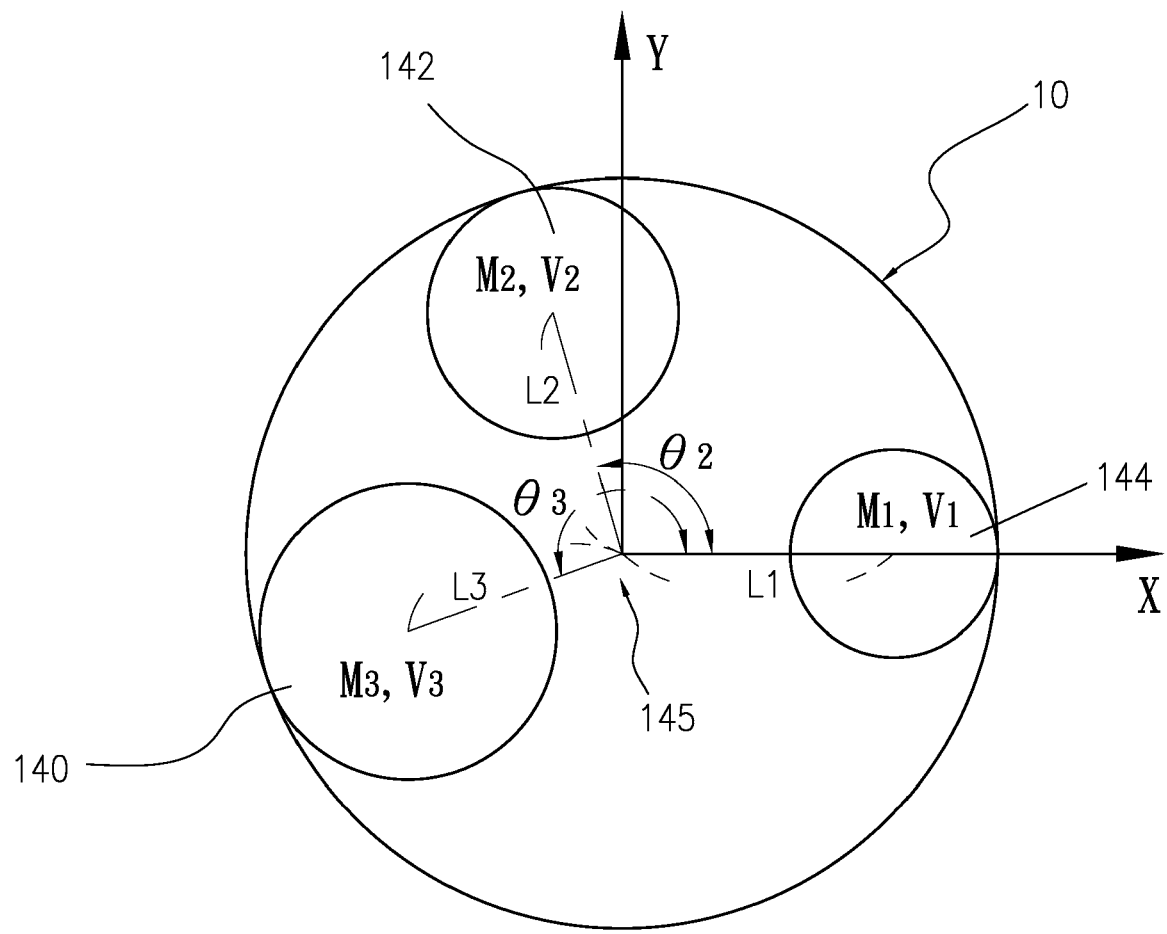
FIG. 1B illustrates an exemplary status of the concentration detector in FIG. 1A.

FIG. 1A is a side view of a concentration detector according to one embodiment of the invention. FIG. 1B illustrates an exemplary status of the concentration detector in FIG. 1A. In FIG. 1A, a fuel supply tank 1 includes a housing 10 with a hollow structure for containing fuels required by a fuel cell, i.e. liquid fuels 12. The liquid fuels 12 may be a methanol solution. The fuel supply tank 1 further includes a first inlet 100, a second inlet 102 and an outlet 104. The first inlet 100 is adapted to inject fuels into the fuel supply tank 1. The second inlet 102 is adapted for injecting an aqueous solution into the fuel supply tank 1 to dilute the concentration of fuels. The outlet 104 is used to drain fuels to an inlet on a flow board (not shown) of a fuel cell.

Figure 2:
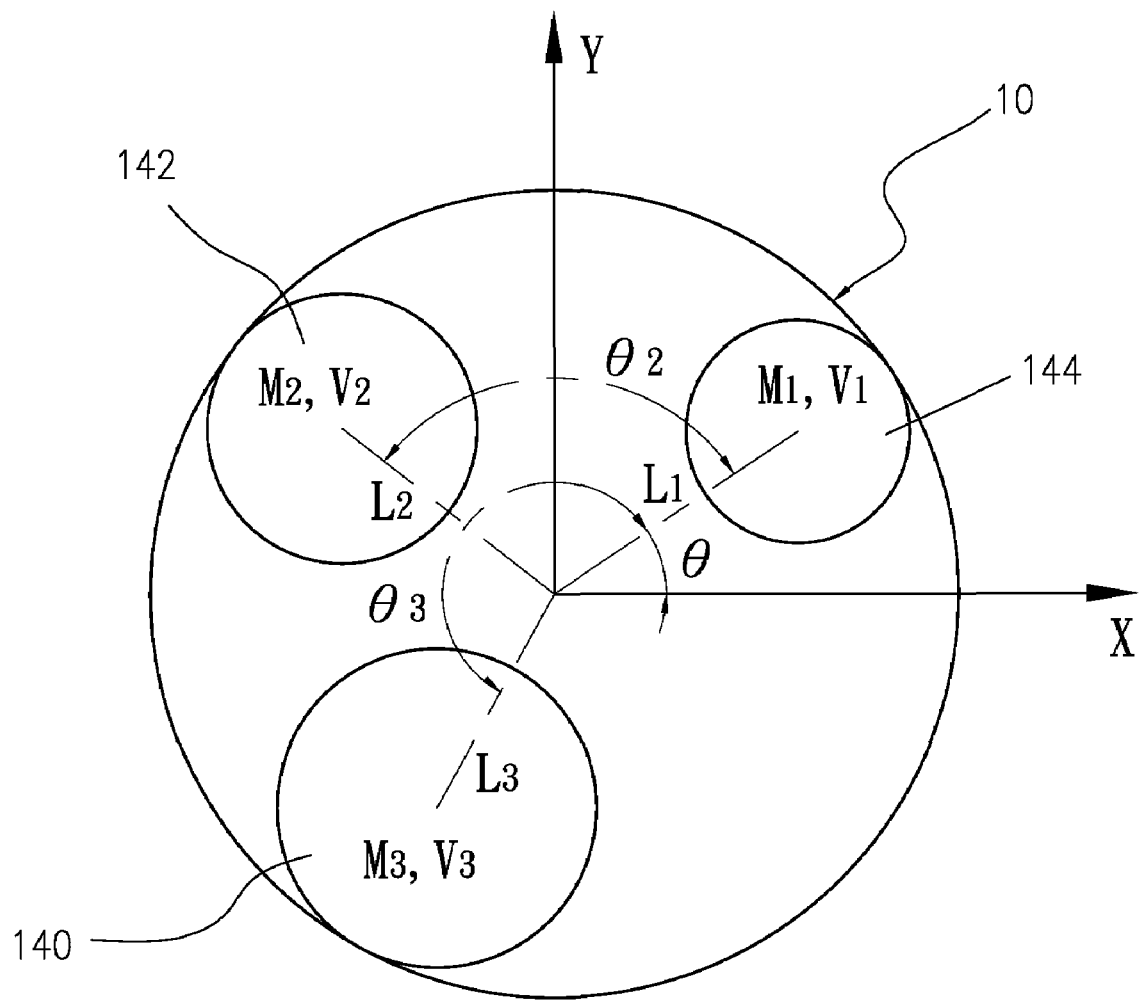
FIG. 2 illustrates another exemplary status of the concentration detector in FIG. 1B.

In one embodiment, a concentration detector is utilized to sense the concentration of the liquid fuels 12 within the fuel supply tank 1. The concentration detector includes a rotating means 14 positioned beneath the level of the liquid fuels 12, and a rotational center 145. The rotating means 14 is rotated with an angle on the X-Y plane as illustrated in FIG. 2. Referring to FIG. 1A, the rotating means 14 includes a first float 140, a second float 142 and a third float 144, which are linked together by rods 146. The first float 140, the second float 142 and the third float 144 may be balls made of anti-corrosive materials. The floats separately have centers of mass, $M_1$, $M_2$ and $M_3$, volume, $V_1$, $V_2$ and $V_3$, as well as specific gravities less than the specific gravity of the liquid fuel 12,$\rho$. With reference to FIG. 1B, the distances between the centers of mass of the floats and the rotational center 145 are $L_1$, $L_2$ and $L_3$, respectively. The center of mass of the first float 140, the center of mass of the second float 142 and the rotational center 145 constitute an included angle $\theta_2$ on the X-Y plane. The center of mass of the first float 140, the center of mass of the third float 144 and the rotational center 145 constitute an included angle $\theta_3$ on the X-Y plane.

FIG. 2 illustrates another exemplary status of the concentration detector in FIG. 1B as the concentration of the liquid fuel 12 is changed. The buoyancy of each floats 140, 142, 144 is different due to the variation of concentration, forcing the rotating means 14 to turn at a rotational angle $\theta$. As a result, the first float 140, the second float 142 and the third float 144 are balanced according to the following torque equation:

$$(M_1-\rho^*V_1)^*L_1^*\cos\theta+(M_2-\rho^*V_2)^*L_2^*\cos(\theta+\theta_2)+(M_3-\rho^*V_3)^*L_3^*\cos(\theta+\theta_3)=0;$$

wherein $M_1$, $M_2$, $M_3$, $V_1$, $V_2$, $V_3$, $L_1$, $L_2$, $L_3$, $\theta_2$, and $\theta_3$ are constants. Based on the torque equation $F(\theta,\rho)=0$, the rotating means 14 is static under the level of the liquid fuel 12. In addition, the rotational angle $\theta$ of the rotating means 14 has only one significant value; hence, the rotational angle θ is determined by the expressed formula below:

[∂F(θ,ρ)/∂θ]>0, where ∂ represents partial differential,

According to the embodiment, the rotational angle θ of the rotating means 14 is detected when the concentration of the liquid fuel 12 is changed. Then, the specific gravity of the liquid fuel 12,ρ, is calculated from the torque equation, F(θ,ρ)=0. Thereafter, the concentration of the liquid fuel 12 is computed. In case the liquid fuel 12 is a methanol solution, the concentration and the specific gravity of the methanol solution can be converted via the comparison table in FIG. 3.

Figure 4:
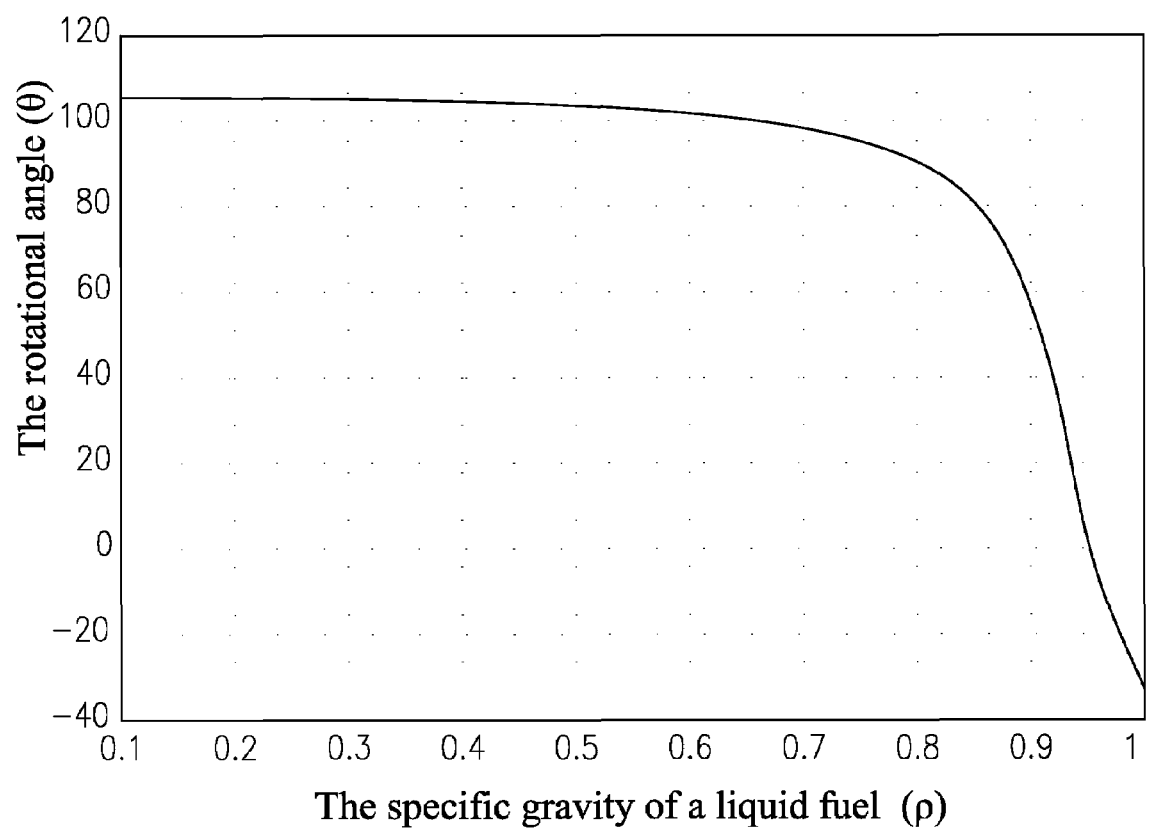
FIG. 4 is a plot showing the specific gravity of a liquid fuel vs. the rotational angle of a rotating means in accordance with a concentration detector of a preferred embodiment of the invention.

FIG. 4 is a plot showing the specific gravity of a liquid fuel ρ vs. the rotational angle of a rotating means θ in accordance with a concentration detector of a preferred embodiment of the invention. The preferred embodiment has some basic data as follows:

$M_1$=1.86(g); $M_2$=1.46(g); $M_3$=2.36(g); $V_1$=2(cm$^3$); $V_2$=1.6 (cm$^3$); $V_3$=2.5(cm$^3$); $L_1$=42(mm); $L_2$=41.7(mm); $L_3$=43 (mm); $θ_2$=112.3°; $θ_3$=206.5°.

It is shown in FIG. 4 that a rotational angle θ corresponds to a specific gravity of a liquid fuel ρ. The curve is sharpest when the specific gravity of a liquid fuel ρ ranges between 0.9 and 1; meanwhile, the rotational angle of a rotating means θ drops from 60° to −30°, of which difference is approximately equal to 100°. It is realized from the experiment that the concentration detector of the preferred embodiment is very sensitive within the range of specific gravity 0.9-1, so the concentration detector is used to detect liquid fuels with a specific gravity ρ from 0.9 to 1, such as the methanol solution in FIG. 3. Because the specific gravity of a liquid fuel ρ is varied with the concentration of the liquid fuel, and the changes of rotational angle θ resulting therefrom is observed by operators or detectors easily. It is thus convenient to identify the concentration of liquid fuels. Aside from the methanol solution, the concentration detector may be applied to other fuel cells employing liquid fuels with different specific gravities.

To sum up, the invention possesses the following features and efficacies, wherein:
1. By setting some parameters as $V_1$=$V_2$=$V_3$, $L_1$=$L_2$=$L_3$, $θ_2$=120°, and $θ_3$=240°, and letting $M_1$, $M_2$ and $M_3$ be geometric series (i.e., $M_1$=r * $M_3$; $M_2$=r2 * $M_3$) in advance may simplify the fabrication of the concentration detector. Consequently, the mass production of the concentration detector is easy and costs less; and
2. It is convenient to identify the concentration of liquid fuels since the concentration detector of the invention is sensitive. Also, the fuel supply tank using such concentration detector is of great ability to detect concentration.

While the invention has been particularly shown and described with reference to the preferred embodiments thereof, these are, of course, merely examples to help clarify the invention and are not intended to limit the invention It will be understood by those skilled in the art that various changes, modifications, and alterations in form and details may be made therein without departing from the spirit and scope of the invention, as set forth in the following claims.

What is claimed is:

1. A concentration detector for detecting a concentration of a liquid fuel in a container, the concentration detector comprising:
   a rotating means positioned underneath a level of a liquid fuel, having a rotational center, and being rotatable at an angle on an X-Y plane, the rotating means comprising:
   at least three floating objects connected with each other, each floating object has a specific gravity less than a specific gravity of the liquid fuel ρ, and the floating objects are balanced according to a torque equation, F(θ,ρ)=0, such that the rotating means is still under the level of the liquid fuel,
wherein while a concentration of the liquid fuel is changed and the angle θ of the rotating means is detected, the specific gravity of the liquid fuel ρ is obtained from the torque equation, F(θ,ρ)=0, and thereby computing the concentration of the liquid fuel.

2. The concentration detector of claim 1, wherein the floating objects are balls.

3. The concentration detector of claim 1, wherein the floating objects comprise a first float, a second float and a third float, wherein the first, second and third floats separately have mass, $M_1$, $M_2$ and $M_3$, as well as volume, $V_1$, $V_2$ and $V_3$, distances between centers of mass of the first, second and third floats and the rotational center are $L_1$, $L_2$ and $L_3$, respectively, and the center of mass of the first float, the center of mass of the second float and the rotational center constitute an included angle $θ_2$ on the X-Y plane, the center of mass of the first float, the center of mass of the third float and the rotational center constitute an included angle $θ_3$ on the X-Y plane.

4. The concentration detector of claim 3, wherein $V_1$=$V_2$=$V_3$, $L_1$=$L_2$=$L_3$, $θ_2$=120°, $θ_3$=240°, and $M_1$, $M_2$ and $M_3$ are geometric series.

5. The concentration detector of claim 3, wherein a function of the torque equation, F(θ,ρ), is F(θ,ρ)=($M_1$−ρ*$V_1$)*$L_1$*cos θ+($M_2$−ρ*$V_2$)*L2*cos(θ+$θ_2$)+($M_3$−ρ*$V_3$)*L3*cos(θ+$θ_3$).

6. The concentration detector of claim 5, wherein the angle θ of the rotating means is determined by a formula [∂F(θ,ρ)/∂θ]>0, where ∂ represents partial differential.

7. The concentration detector of claim 1, wherein the container is a fuel supply tank to provide a fuel for a fuel cell.

8. The concentration detector of claim 7, wherein the liquid fuel is a methanol solution.

9. The concentration detector of claim 8, wherein the floating object is made of an anticorrosive material.

10. The concentration detector of claim 7, wherein the fuel supply tank further comprises a first inlet for injecting a fuel into the fuel supply tank.

11. The concentration detector of claim 10, wherein the fuel supply tank further comprises a second inlet for injecting an aqueous solution into the fuel supply tank.

12. The concentration detector of claim 11, wherein the fuel supply tank further comprises an outlet for draining the fuel to an inlet of a flow plate of the fuel cell.

13. A fuel supply tank for a liquid fuel cell, the fuel supply tank comprising:
   a housing including a hollow structure for containing a liquid fuel; and
   a concentration detector disposed inside the housing to detect a concentration of the liquid fuel, the concentration detector comprises a rotating means positioned underneath a level of the liquid fuel, having a rotational center, and being rotatable at an angle θ on an X-Y plane, and the rotating means comprising:
   at least three floating objects connected with each other, each floating object has a specific gravity less than a specific gravity of the liquid fuel ρ, and the floating objects are balanced according to a torque equation, F(θ,ρ)=0, such that the rotating means is still under the level of the liquid fuel,
wherein the concentration of the liquid fuel is changed and the angle θ of the rotating means is detected, the specific gravity of the liquid fuel $\rho$ is obtained from the torque equation, $F(\theta,\rho)=0$, and thereby computing the concentration of the liquid fuel.

14. The fuel supply tank of claim 13, wherein the floating objects are balls.

15. The fuel supply tank of claim 13, wherein the floating objects comprise a first float, a second float and a third float, wherein the first, second and third floats separately have mass, $M_1$, $M_2$ and $M_3$, as well as volume, $V_1$, $V_2$ and $V_3$, distances between centers of mass of the first, second and third floats and the rotational center are $L_1$, $L_2$ and $L_3$, respectively, and the center of mass of the first float, the center of mass of the second float and the rotational center constitute an included angle $\theta_2$ on the X-Y plane, the center of mass of the first float, the center of mass of the third float and the rotational center constitute an included angle $\theta_3$ on the X-Y plane.

16. The fuel supply tank of claim 15, wherein $V_1=V_2=V_3$, $L_1=L_2=L_3$, $\theta_2=120°$, $\theta_3=240°$, and $M_1$, $M_2$ and $M_3$ are geometric series.

17. The fuel supply tank of claim 15, wherein a function of the torque equation, $F(\theta,\rho)$, is $F(\theta,\rho)=(M_1-\rho*V_1)*L_1*\cos\theta+(M_2-\rho*V_2)*L_2*\cos(\theta+\theta_2)+(M_3-\rho*V_3)*L_3*\cos(\theta+\theta_3)$.

18. The fuel supply tank of claim 17, wherein the angle $\theta$ of the rotating means is determined by a formula $[\partial F(\theta,\rho)/\partial\theta]>0$, where $\partial$ represents partial differential.

19. The fuel supply tank of claim 13, wherein the liquid fuel is a methanol solution.

20. The fuel supply tank of claim 19, wherein the floating object is made of an anticorrosive material.

21. The fuel supply tank of claim 13, wherein the housing further comprises a first inlet for injecting the liquid fuel into the fuel supply tank.

22. The fuel supply tank of claim 21, wherein the housing further comprises a second inlet for injecting an aqueous solution into the fuel supply tank.

23. The fuel supply tank of claim 22, wherein the housing further comprises an outlet for draining the liquid fuel to an inlet of a flow plate of the liquid fuel cell.

* * * * *